United States Patent [19]

Yao et al.

[11] Patent Number: 4,805,624
[45] Date of Patent: Feb. 21, 1989

[54] LOW-POTENTIAL ELECTROCHEMICAL REDOX SENSORS

[75] Inventors: Shang J. Yao; Sidney K. Wolfson, Jr., both of Pittsburgh, Pa.

[73] Assignee: The Montefiore Hospital Association of Western PA, Pittsburgh, Pa.

[21] Appl. No.: 37,976

[22] Filed: Apr. 14, 1987

Related U.S. Application Data

[63] Continuation of Ser. No. 774,281, Sep. 9, 1985, abandoned.

[51] Int. Cl.$^4$ ............................................. A61B 5/00
[52] U.S. Cl. .................................... 128/635; 204/406
[58] Field of Search ............................... 128/635-640; 204/1 K, 5 T, 403, 406, 422, 415

[56] References Cited

U.S. PATENT DOCUMENTS

| | | | |
|---|---|---|---|
| 4,276,144 | 6/1981 | Hahn et al. | 128/635 |
| 4,340,458 | 7/1982 | Lerner et al. | 204/1 T |
| 4,396,464 | 8/1983 | Lerner et al. | 128/635 |
| 4,431,004 | 2/1984 | Bessman et al. | 128/635 |
| 4,452,672 | 6/1984 | Parker et al. | 128/635 |
| 4,458,686 | 7/1984 | Clark, Jr. | 128/635 |
| 4,467,811 | 8/1984 | Clark, Jr. | 128/635 |
| 4,495,051 | 1/1985 | Fujita et al. | 204/415 |
| 4,508,598 | 4/1985 | Giner | 128/635 |
| 4,545,863 | 10/1985 | Yeager et al. | 204/415 |
| 4,547,280 | 10/1985 | Karasawa et al. | 204/415 |

OTHER PUBLICATIONS

Blackshear, P. J., Rohde, T. D., Grotting, J. C., Dorman, F. D., Perkins, P. R., Varco, R. L., Buchwald, H. *Diabetes.* 1979; 28: 634–639.

Bojsen, J., Deckert, T., Kolendorf, K., Lorup, B. *Diabetes.* 1979; 28: 974–979.

Champion, M. C., Shepherd, G. A. A., Rodger, N. W., Dupre, J. *Diabetes.* 1980; 29: 206–212.

Clemens, A. H., *Diabetes Care.* 1980; 3: 359–361.

Chang, K. W., Aisenberg, S., Soeldner, J. S., Hiebert, J. M. *Trans. Am. Soc. Artif. Intern. Organs.* 1973; 19: 352–360.

Soeldner, J. S., Chang, K. W., Hiebert, J. M., Aisenberg, S. *Diabetes.* 1973; 24: 294, (Supplement 1).

Gough, D. A., Aisenberg, S., Colton, C. K., Giner, J., Soeldner, J. S. *Horm. Metab. Res. Suppl.* 1977; 7: 10–22.

Nalecz, M., Lewandowski, J., Werynski, A., Zawicki, I. *Artificial Pancreas.* 1978; 2: 305–309.

Gough, D. A., Anderson, F. L., Giner, J., Colton, C. K., Soeldner, J. S. *Anal. Chem.* 1978; 50: 941–944.

Rao, J. R., Richter, G. J., Luft, G., von Sturm, F. *Biomater. Med. Devices Artif. Organs.* 1978; 6(2): 127–149.

(List continued on next page.)

*Attorney, Agent, or Firm*—The Dulin Law Firm

[57] ABSTRACT

Improved low-potential electrochemical sensors and method for rapid, accurate, in vitro and in vivo measurement of the concentration of carbohydrates in organic or biological fluids by cyclic voltammetric or coulometric scan within a restricted voltage domain and identifying one or more oxidation and/or reduction current peaks, with the concentration of the carbohydrate being a linear function of the current output. Two well defined, sharp, distinctly separated, specific, reproducable and interference-free peaks have been discovered in the low-potential voltage domain of −0.9V to −0.2V, cathodic reduction Peak 1 and anodic oxidation Peak 2 in the range of −0.70V to −0.90V. The scan is pulsed or a steady sweep, and sensitivity increases with increased scan rate in the range of 30–50 mV/sec. Pulses may range on the order of 20–50 millisecond in duration, and sampling during the last 1.5 milliseconds of the pulse restricts values to pure oxidation/reduction currents. Cyclic and/or pulsed scanning regenerates the electrodes making the sensor drift free. A system is disclosed employing the sensor as part of an implantable insulin pump which is microprocessor controlled, thus functioning as an artificial pancreas. The sensors can also be used in bedside monitoring systems as an indwelling sensor introduced by catheterization, for in-line extracorporeal shunt systems, or for non-invasive measurement of carbohydrate levels.

18 Claims, 5 Drawing Sheets

OTHER PUBLICATIONS

Marincic, L., Soeldner, J. S., Colton, C. K., Giner J., Morris, S. J. *Electrochem. Soc.* 1979; 126: 43–49.

Lerner, H., Giner, J. Soeldner, J. S., Colton, C. K., *J. Electrochem. Soc.* 1979; 126: 237–242.

Marincic, L. Soeldner, J. S., Giner, J., Colton, C. K. *J. Electrochem. Soc.* 1979; 126: 1687–1692.

Lemke, K., Gorner, M. *Bioelectrochem. Bioenerg.* 1981; 8: 115–124.

Updike, S. J., Hicks, G. P. *Nature.* 1967; 214: 986–988.

Bessman, S. P., Schulz, R. D., *Trans. Am. Soc. Artif. Intern. Organs.* 1973; 19: 361–364.

Silver, I. A. In: Kessler, M., Clark, L. C., Jr., Lubbers, D. W., Simon, W., *Ion and Enzyme Electrodes in Biology and Medicine.* vol. 5: Munchen–Berlin–Wien: Urban and Schwarzenberg, 1976: 189.

Layne, E. C., Schultz, R. D., Thomas, L. J., Slama, G., Sayler, D. F., Bessman, S. P. *Diabetes.* 1976; 25: 81–89.

Bessman, S. P., Schultz, R. D. *Horm. Metab. Res.* 1972; 4: 413–417.

Clarke, W. L., Santiago, J. V. *Artificial Organs.* 1977; 1: 78–82.

Liu, C. C., Wingard, L. B., Wolfson, S. K., Jr., Yao, S. J., Drash, A. L., Schiller, J. G. *Bioelectrochem. Bioenerg.* 1979; 6: 19–26.

Clemens, A. H., Chang, P. H., Myers, R. W., *Horm. Metab. Res.* 1977; 7: 23—33.

Lerner, H., Giner, T., Soeldner, J. S., Colton, C. K. Presented at the American Institute of Chemical Engineers, 1981 Annual Meeting, New Orleans, Nov. 8–12, 1981; (Abstract No. 113g, program page T-184).

Guyton, J. R., Chang, K. W., Aisenberg, S., Soeldner, J. S. *Med. Instr. 1975; 9: 227–232.*

Giner, J., Marincic, L., Soeldner, J. S., Colton, C. K., *J. Electrochem. Soc.* 1981; 128: 2106–2114.

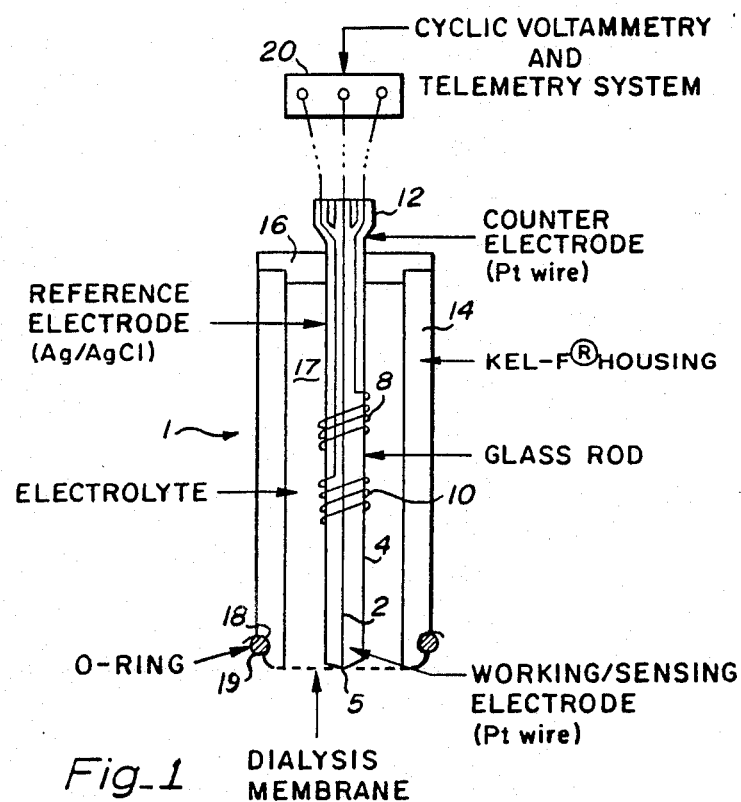
Fig_1
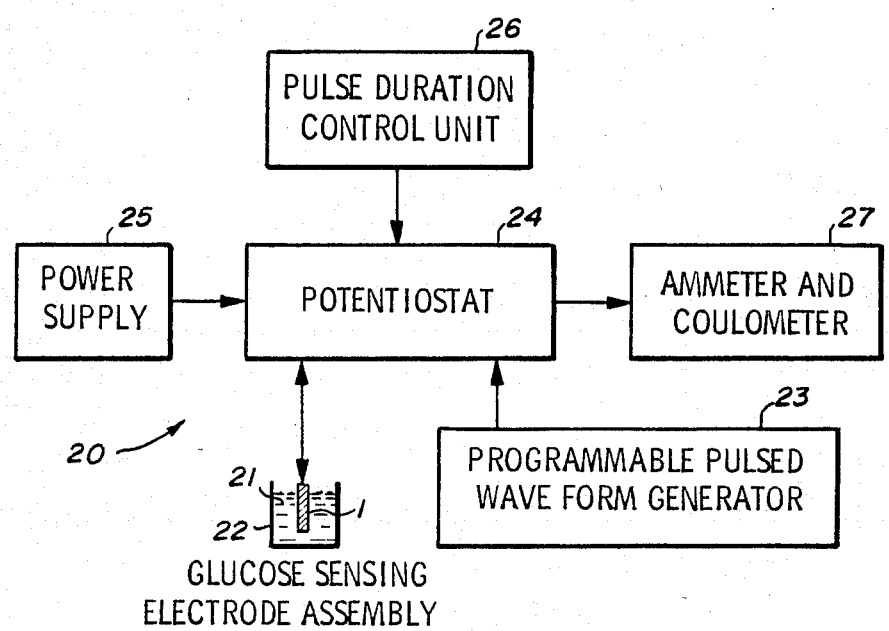
Fig_2

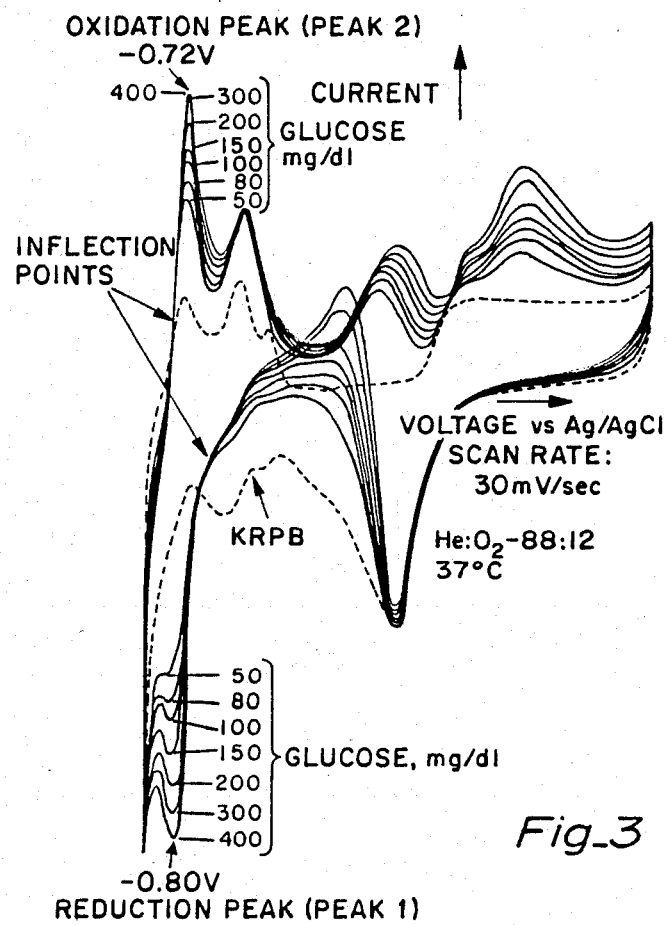
Fig_3
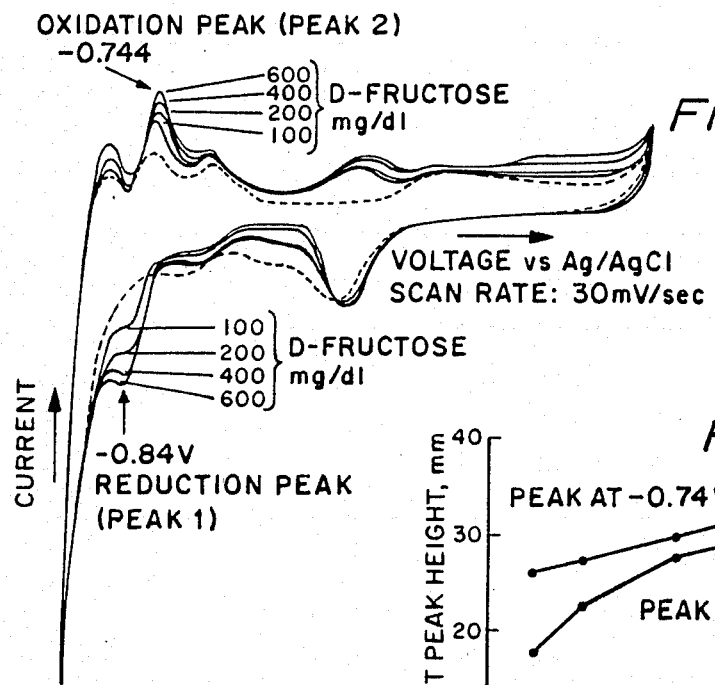
Fig_4a
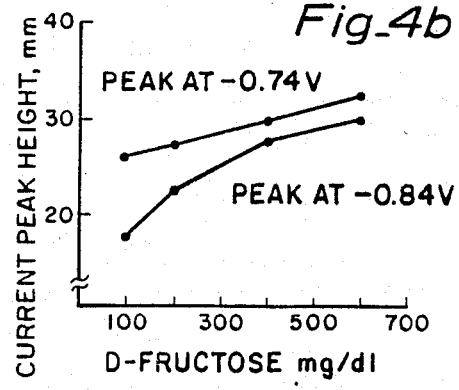
Fig_4b

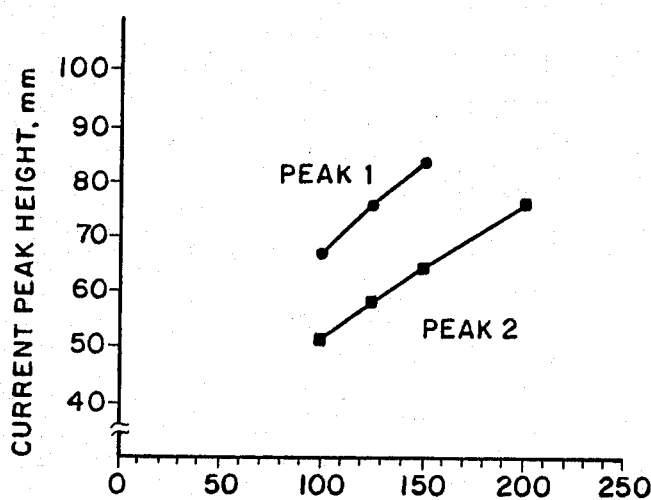
Fig_5
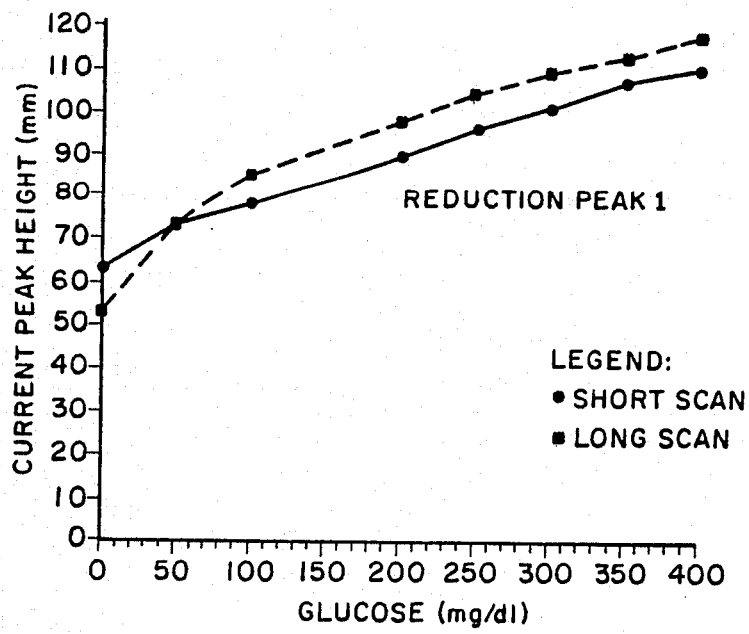
Fig_6

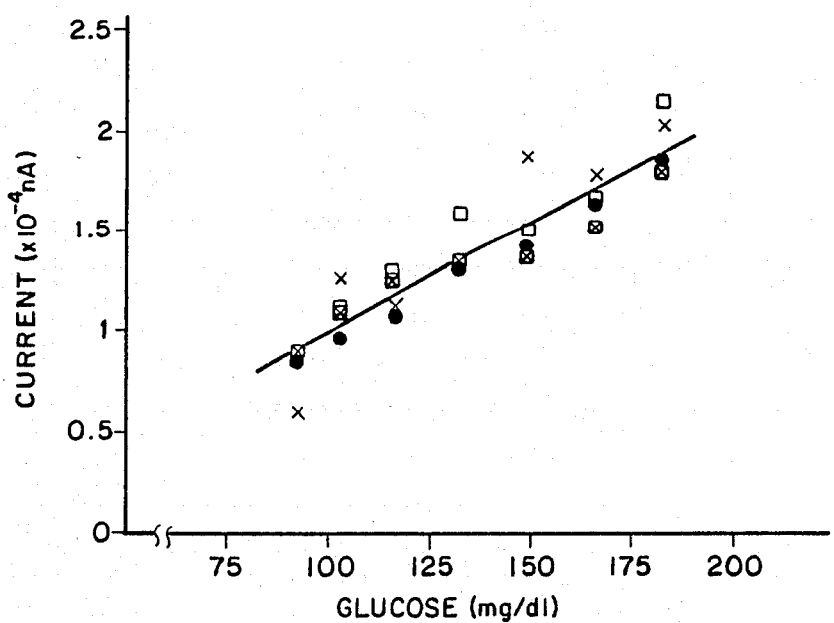
Fig_9
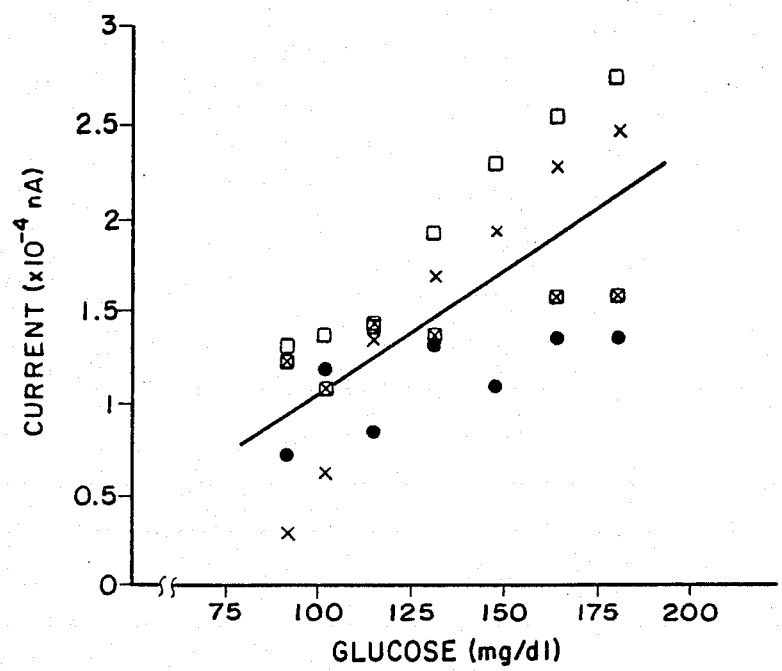
Fig_10

LOW-POTENTIAL ELECTROCHEMICAL REDOX SENSORS

This is a continuation of application Ser. No. 774,281, filed Sept. 9, 1985, by us for Low Potential Electrochemical Redox Sensors and Method, abandoned.

FIELD

This invention relates to biomedical redox sensors and methods of operation, more particularly to carbohydrate sensors (e.g. glucose sensors) of sufficiently fast response to be continuous reading sensors which have high resolution (accurate enough to resolve changes as small as 5 mg/dl in blood glucose concentration) and which are free of baseline and sensitivity drift. By the method of operation of the invention, the sensor can positively characterize glucose and other carbohydrates in organic and biologic fluids, especially tissue fluids and vascular system (direct blood contact) environments, making possible an in vivo implantable closed-loop glucose sensing and continuous insulin/glucagon infusion delivery system, i.e., an artificial pancreas (artificial Beta-cell), which in human subjects permits more normally unregimented activity patterns of rest, meals, work, play and exercise.

BACKGROUND

In the past few years, extensive efforts have been made toward the development of implantable prostheses and bedside equipment which could continuously control the insulin infusion rate to maintain an appropriate blood glucose level for the patient [1-4]. These devices are called the artificial pancreas or artificial Beta-cell.

The major components required for a system of complete metabolic control are: an insulin infusion pump; an accurate, selective and continuous glucose concentration sensing element; and a logic control device. Several pumps for open-loop programmed insulin infusion have been developed and are now under clinical evaluation. Microminiature, solid state microprocessor computer devices are available or developable as being within the state of the art.

However, a glucose-selective, long-term, and reproducible detector essential for an implantable sensing element has not been available. The development of such a sensor would constitute a breakthrough for both the clinical practice and basic investigation of diabetes and its associated complications. Its absence is the missing link for workable closed-loop insulin infusion systems.

Uses for such a detector would include benchtop analyses, bedside monitoring, and the implanted "artificial pancreas." Significant effects of improved metabolic control on the incidence of complications in diabetes millitus will not be seen until an implantable, closed-loop insulin infusion system with near physiologic performance is available.

Several approaches to the development of an implantable glucose sensor have been explored. These include (1) electrochemical sensors such as those employing amperometric and potentiometric detectors [5-14, 25-27]; (2) enzyme sensors with enzyme coupled to an electrochemical detector [15-22]; and (3) optical sensors [8]. The main difficulties encountered in the development of the conventional electrochemical sensors are twofold: (1) insufficient selectivity for glucose; and (2) poor reproducibility. Lack of reproducibility means the sensor is neither continuous nor reliable, even in intermittant operation. Enzyme sensors suffer from the loss of enzyme activity due to "poisoning" and poor long-term stability. The optical methods are limited by the fact that only minimal optical rotation of the plane of polarization is observed for glucose levels of less than 400 mg/dl [8]. But it is in this vital range (below 400 mg/dl) that medical interest resides. In fact the body ordinarily operates in the much narrower range of 70-150 mg/dl.

Recently, an implantable electrochemical glucose sensor based on a potentiodynamic approach has been studied [11-13, 23]. Though the sensing is relatively reproducible in a glucose solution, it suffers greatly by the inhibition of added co-reactants such as amino acids and urea [9, 11-13, 24-27]. A "compensated net charge method" of signal analysis has been proposed to counter this interference. Preliminary experiments have been reported in which the compensated net charge approach provided some improvement in both sensitivity to glucose and insensitivity to interfering co-reactants [23].

Electrochemical detection could be an answer to glucose (and other carbohydrate) monitoring provided that the sensor is glucose-selective, sensitive, and reproducible (reliable and continuously operating). Moreover, the detecting electrode itself or associated components must not dissolve into body fluid and no toxic substances should be generated. The detector should be susceptible to miniaturization, and provide a sufficient output that can be processed and/or enhanced to be utilized by a controlled infusion system.

The present invention satisfies this unfilled need in the art by providing a carbohydrate sensor that operates by pulsed voltammetry or pulsed coulommetry in the far negative potential range ($-0.90$ V to $-0.20$ V) to detect two well defined, distinctly separated, sharp oxidation and reduction (redox) peaks of a reversible simple oxidation-reduction (redox) couple involving a direct, single electron transfer process under diffusion control that is not interfered-with by other oxidizable compounds present in the fluids. The signal exhibits a linear relationship with respect to concentration in the useful physiologic glucose concentration range of 50-400 mg/dl, the voltages of which signals do not shift with changes in glucose concentration, thus permitting continuous, highly selective, reproducible, reliable concentration sensing.

THE INVENTION

Objects

It is among the objects of this invention to provide an improved electrochemical carbohydrate sensor particularly useful for accurate, continuous, drift-free, highly selective, reproducible sensing of glucose in solutions (both in vivo and in vitro) without interference from other organic compounds.

It is another object of this invention to employ the sensor in combination with other elements, including a pulse source, microprocessor and an infusion pump as an implantable closed-loop pancreas (artificial Beta-cell).

It is another object of this invention to provide an electrochemical method of continuously determining carbohydrate (particularly glucose) concentrations in solutions with a specificity that permits accurate measurement for a variety of diagnostic and treatment procedures, e.g., bedside monitors emplaced in a patient by catheterization.

It is another object of this invention to provide an improved cyclic voltammetric scanning method for precise determination of concentrations of various carbohydrates in solutions, which determination is specific to the carbohydrate desired to be measured.

It is another object of this invention to provide such a method by which the sensitivity can be adjusted to cover the biologically significant operating range of carbohydrate concentration, and by which the sensor can be made drift free.

It is another object of this invention to provide such a sensor and method which permit accurate, reproducible, continuous, fast, and highly specific readings for bedside monitors, extracorporeal shunts, noninvasive carbohydrate sensing or the like for a variety of biological and medical analyses and treatments, including high performance liquid chromatography.

It is another object of this invention to provide a method of identifying one or more oxidation or reduction current peaks which exhibit a linear function with respect to concentration and are specific to carbohydrates within a limited scanned electrochemical domain, which method permits a wide variety of chemical, biological and medical analyses, diagnoses and treatments.

Still further and other objects will be evident in the descriptions and drawings which follow.

SUMMARY

The invention involves improved electrode sensors for in vitro or in vivo measurement of the concentration of glucose and other carbohydrates in organic or biological fluids by cyclic voltammetric or coulommetric scan within a restricted voltage domain or part thereof, identifying one or more oxidation and/or reduction current peaks within the chosen domain, and determining the concentration as a linear function of the current output. The scan can be a steady sweep or pulsed, and the sensitivity increases with increased scan rate. Cyclic scanning alone or in combination with pulsing effectively regenerates the electrodes, making the sensor drift free. The peaks are specific to the particular carbohydrate (glucose, fructose, mannose, and the like). In the case of glucose, the linear range, being between 0–400 mg/dl of glucose, permits in vivo implantation of the sensor in conjunction with an insulin pump, the combination being an artificial pancreas. The linear ranges for fructose and mannose are the same, 0–600 mg/dl.

Employing cyclic voltammetry of carbohydrates in solution, we have discovered two well-defined redox current peaks in a very low potential region by use of a smooth Pt sensing electrode, preferably a Pt wire, with a Pt counter electrode and an Ag/AgCl reference electrode. At 37° C., these peaks are for glucose, a cathodic reduction peak at −0.80 V vs. Ag/AgCl (called by us "Peak 1"), and an anodic oxidation peak at −0.72 V vs. Ag/AgCl (called by us "Peak 2"). For fructose, the peaks are at −0.84 V (Peak 1) and −0.74 V (Peak 2) respectively, and the latter is linear to 600 mg/dl. As shown by voltammograms, the current signals arising from strongly adsorbed carbohydrate species (e.g., glucose) at a scan rate of from 30–50 mV/sec (with 30 mV/sec being preferred) also demonstrate inflection points, which are voltages at which the oxidation and reduction currents switch, indicating simple redox chemistry with no interference from substances which can only be oxidized or reduced at higher potentials.

The peaks are well defined, substance specific, sharp, distinctly separated, and reproducible, and together form a reversible redox couple. We have found that the current of these peaks varies linearly with the concentrations of the carbohydrate (e.g., glucose, mannose and fructose). Unlike other observed signals reported in all other published reports [5–14, 25–27] at less negative or positive potential regions, the peak voltages do not shift with variations of concentration.

The linearity of current to concentration is in a clinically important range, the range of 50–400 mg/dl, which permits monitoring for diabetes control, and the sensor response is rapid, drift free and reproducible, so that continuous monitoring for in vivo implantation is entirely feasible.

Unlike other reported peaks, we have also found that at this low potential (far negative) region of −0.9 V to −0.2 V, amino acids, urea and other substances present in serum or serum dialysate will not inhibit the signals, particularly the reduction Peak 1 (−0.80 V for glucose and −0.84 V for fructose at 37° C. vs. Ag/AgCl). In contrast, "peaks" earlier reported [5–14, 25–27] at +0.70 V, −0.43 V, −0.58 V, −0.62 V, −0.65 V; (1) are not true peaks; (2) are not true peak locations; (3) are peaks that shift with changes in concentration; or (4) represent reactions interfered-with or complicated by other substances in the solution (e.g., dialysate fractions).

While we do not wish to be bound by theory, this −0.80 V signal may be the cathodic reduction of $H^+$ which would be generated as a product of the anodic oxidation of an OH group of a carbohydrate (e.g., glucose) at −0.72 V in the anodic portion of the scan. The linearity demonstrates that the redox couple is under diffusion control. Our analysis shows the peak currents agree with the Randles-Sevcik equation:

$$i_p = k n^{\frac{3}{2}} A D^{\frac{1}{2}} C v^{\frac{1}{2}}$$

Bard, A. J., Faulkner, L. R., *Electrochemical Methods—Fundamentals and Applications,* John Wiley & Sons, New York (1980). The peak-to-peak separation at a scan rate of 30 mV/sec is 0.08 V at 37° C. Further, the absence of multiple, overlapping peaks indicates the chemistry is a simple redox.

We believe the reaction can be considered a direct, reversible, one electron transfer process which does not involve non-electrochemical or secondary reactions, and is thus highly selective and reproducible—a vital characteristic for continuous clinical, in vitro or in vivo monitoring. In the case of glucose, for example, glucose molecules may be adsorbed or interact with adsorbed hydrogen species at the smooth Pt electrode at low anodic potentials, and produce hydrogen desorption or oxidation currents. The cathodic reduction of glucose would be taking place at the −0.80 V potential, the potential of hydrogen evolution.

The electrochemical redox sensor employed in this invention comprises a working (detecting) electrode (W), a counter electrode (C), and a reference electrode (R). The electrodes may be, but are not required to be, covered together or separately by a semipermeable protective membrane such as a regenerated cellulose film, hydrogel or the like. For example, we expect the membrane could be omitted in the case of suitable in vitro systems or when implanted in vivo in tissue spaces not containing high proteins or other inhibitor or electrode poisoning macromolecules. The working (W) and counter electrodes (C) are smooth Pt, (or other metals disclosed herein) such as a disc of area 1 cm$^2$, a wire, or a deposited metal film, while the reference electrode may be a saturated KCl-Ag/AgCl electrode, a chlorided silver wire, or a deposited silver film. The metal films may be deposited on any suitable substrate, e.g. ceramic, plastic, fused silica or, in the case of in vivo implantation, any tissue compatible material. Other conventional reference electrodes can be used with appropriate interfaces.

We employ pulsed coulommetry or pulsed voltammetry by applying variable and pulsating potentials (voltage). The charge (coulombs) and/or current (amperes) generated by direct or indirect redox processes of reacting species at the W surface are recorded as highly selective signals specific to the substance or species concerned. The amplitude of the current signals are linearly dependent upon the carbohydrate (CHO) concentration. The electrodes of the invention can thus be calibrated against known solution concentrations. Further, comparison of the electrode output for solutions of known CHO concentrations, to the output for unknown test specimen samples (or tissue implantations), permits direct determination of the CHO concentrations of those test specimens. This may be used for in vitro and in vivo determination of carbohydrate concentration in the blood stream or tissue fluids, such as an in-line glucose sensor in a batch sampling technique, or as an implantable glucose sensor.

An important aspect of the invention is the use of cycling of the potential scan to actually regenerate the W surface during each period of the scan, thus extending the life of the implantable sensor. The use of pulsed sequences at the identified voltages (−0.80 V and −0.72 V) for very short periods, i.e., 20–50 milliseconds, provides additional anodic and cathodic regenerative cleaning of the W electrode surface.

The scope of this invention includes the method and apparatus for the determination of carbohydrates, e.g., glucose, fructose, mannose, and the like. The method and apparatus can be for in vitro and in vivo carbohydrate determinations, clinical or industrial monitoring of carbohydrates, analytical determination of carbohydrates by high performance liquid chromatography, and the like. The electrode and system of this invention are extremely useful for the noninvasive determination of carbohydrates in exterior tissue fluid, such as in the conjunctiva under the eyelid or in the oral cavity, sugar in the extracorporeal blood stream (in-line) or cerebrospinal fluid, in urine, and in implanted tissue sites or in indwelling bloodstream electrodes (besides monitors).

The electrode metals may include, but are not limited to: smooth Pt, Pt-black, Pd, Pd-black, Rh, Rh-black, alloys such as Pt-Ir, Pt-Pd, Pt-Rh, Pd-Rh, and the like. The fluids or samples include but are not limited to: both biological or organic fluids and tissues in both living and dead animals and humans, vegetables, plants, soils, sewage, lakes, glaciers, rivers, sea waters, and the like. Body millieu include, but are not limited to: blood, tissue, tears, urine, cerebrospinal fluid, laboratory-prepared simulated body fluids, buffer solutions, and the like.

In the implanted in vivo artificial pancreas (artificial Beta-cell) system of this invention, the implanted glucose sensor assembly (employing a power source and pulse generator) provides signals to a microprocessor which processes the signals and commands a delivery system to meter-out or permit infusion of insulin, glucose and/or glucagon to regulate carbohydrate metabolism and compensate for imbalances in glucose levels in the patient. Likewise, the glucose sensor can be used in an in-line extracorporeal shunt system, bedside monitors, or for noninvasive measuring systems.

As noted above the well defined cathodic and anodic peaks lie in the range of about −0.70 V to −0.90 V, depending on carbohydrate species. For Peak 1 the values are: −0.80 V for glucose (dextrose); −0.84 V for fructose; and −0.84±0.02 V for mannose under the conditions shown. For Peak 2 the values are: −0.72 V for glucose (dextrose); −0.74 V for fructose; and −0.75±0.01 V for mannose. For each different carbohydrate the peaks are distinct thus making possible distinguishing the concentrations of each of several carbohydrates in a test specimen. It should be understood that we expect the positions of these peaks will be shifted somewhat for a change of conditions from those disclosed herein as the best mode, e.g., temperature changes, electrolyte type, sample type or tissue millieu, different electrode metal, and the like. However, once the peaks are located within the low potential, far negative region for a given set of conditions, the peak(s) do not shift with changes in concentration of carbohydrate being sampled.

DRAWINGS

The invention is illustrated in more detail in the drawings in which:

FIG. 1 shows in partial section view one embodiment of the sensor of this invention in which the wire elements may be replaced with disc or film elements as described herein;

FIG. 2 is a schematic of the apparatus for low-potential pulsed coulommetry and voltammetry used in this invention;

FIG. 3 is a combined cyclic voltammogram employing the sensor of FIG. 1 in the system of FIG. 2 detecting increasing concentrations of glucose, with the −0.72 V oxidation peak and −0.80 V reduction peak being clearly evident;

FIG. 4a is a combined cyclic voltammogram of the type shown in FIG. 3 for fructose showing Peak 1 at −0.84 V and Peak 2 at −0.74 V;

FIG. 4b is a plot of current vs. concentration of fructose data from FIG. 4a showing a linear relationship out to 600 mg/dl, well beyond the clinical range;

FIG. 5 is a plot of the redox current peak heights vs. glucose concentrations in human serum dialysate illustrating the linear relationship between current and serum glucose concentration, and is notable as showing no inhibition of peak sensing;

FIG. 6 is a plot of current peak height for the reduction peak at −0.80 V vs. glucose concentration for both long and short scan rates;

FIG. 9 is a plot of concentration of glucose in the ultrafiltrate of human serum using the sensor system and method of this invention;

FIG. 10 is a plot of glucose concentration vs. current Peak 2 using the sensor system and method of this invention.

DETAILED DESCRIPTION OF THE PREFERRED EMBODIMENT

Figure 7:
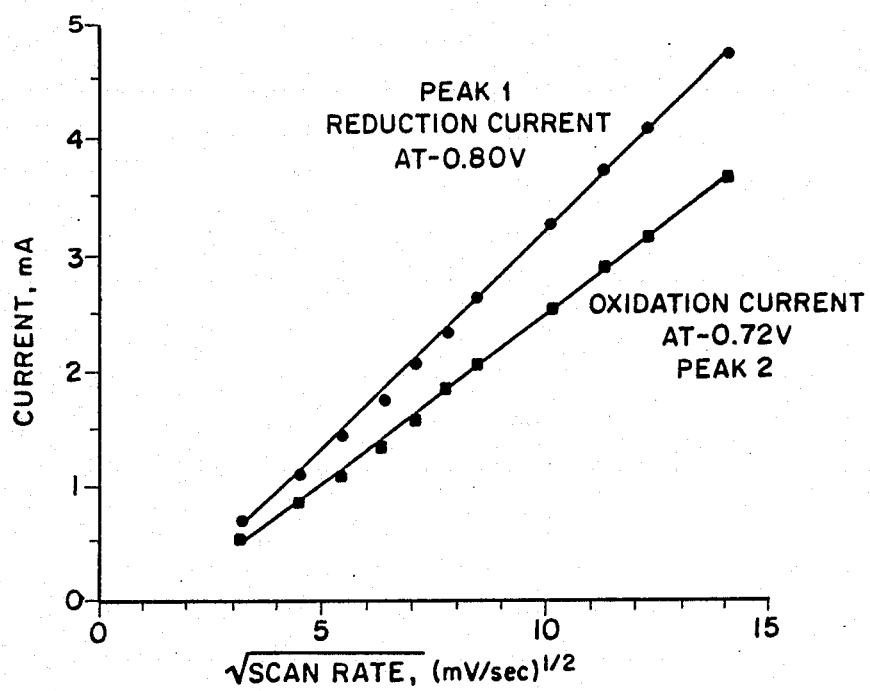
FIG. 7 is a plot of the current of Peaks 1 and 2 vs. the square root of scan rates demonstrating the linear relationship.

The invention is more particularly described below in connection with the preferred embodiment which illustrates, without limitation, the principles of the invention. While we discuss glucose in most detail, the comments apply equally to other carbohydrates, such as (but not limited to) fructose and mannose ( see e.g., FIGS. 4a and 4b) for their respective Peaks 1 and 2.

FIG. 1 shows in schematic the improved electrode assembly 1 of this invention in which a smooth platinum wire 2 is embedded in a glass rod 4 to form the working/sensing electrode. The bottom tip 5 of the platinum wire is exposed and is in contact with the inner surface of the semipermeable membrane 6.

Wound around the exterior surface of the glass rod 4 is a first counter electrode 8 of smooth platinum wire, and a second reference electrode 10. The two electrode windings are spaced from each other, and are medial of the two ends of the glass rod with the reference electrode being between the counter electrode and the lower end of the glass rod. The lead wires of all three electrodes run up through the glass rod, and emerge through cap 12 which keeps them spaced apart so that they do not short out. The three leads are connected to the cyclic voltammetry and telemetry system 20 which is described in more detail with reference to FIG. 2.

The glass rod electrode holder 4 is disposed within a tubular housing 14, preferably of glass or an inert plastic material such as polytetrafluoroethylene or trichlorofluoroethylene. Apertured plug 16 retains the electrode rod 4 rigidly in position. The lower end of the electrode rod 4 may be held in position by spacers if required. The plug may also be made of the same inert material as the housing 14.

The lower end of the housing wall has a groove 18 to receive an O-ring 19 which retains the membrane 6 across to lower opening of the housing 14. The annular space is filled with a Krebs-Ringer phosphate buffer (KRPB), pH 7.4.

The semipermeable membrane 6 is typically a dialysis-type or ultrafiltration-type membrane, and is selected to admit glucose or other low molecular weight carbohydrate to the working electrode 2, while excluding both middle and high molecular weight substances. suitable membrane materials include cellulose dialysis membranes, hydrogel films, or comparable films.

FIG. 2 is a schematic diagram of the apparatus system 20 employed in this invention for the low potential pulsed cyclic voltammetry or coulommetry. The electrode system 1 as described above in detail with respect to FIG. 1 is immersed in a solution 21 containing various concentrations of glucose. For in vitro studies, a solution is contained in beaker 22. For the in vivo system, this may be implanted, or the body fluid being tested can be passed through an extracorporeal shunt, in which case 22 represents a cuvette or other chamber containing the miniature electrode assembly 1. Digital function generator 23 provides a variable voltage driving mechanism for potentiostat 24 pursuant to the predetermined cyclic program. Power is supplied to the potentiostat by power supply 25, and the scan cycle is controlled by the scan and pulse duration control unit 26. We prefer to use an ECO Model 567 digital function generator and an ECO 549 potentiostat. The reference electrode was Ag/AgCl from In Vivo Metric Systems, Haroldsburg, Calif. The test examples herein were performed at 37° C. at scan rates between 30-50 mV/sec although we expect a broader scan rate to produce equivalent results. The domain for scanning ranged from −0.2 V to −0.90 V.

While we can use normal and differential pulse voltammetry, we prefer to use square wave voltammetry as we can sample the current at Peaks 1 and 2 more quickly, and accordingly more nearly continuously. Normal and differential pulse techniques typically run at scan rates of 1-10 mV/sec. The square wave voltammetry permits scan rates up to 1 V/sec or more, thus permitting a determination of glucose concentration in a matter of seconds. Accordingly, we employ a programmable pulse waveform generator 23 for the input pulses (of duration on the order of 20-50 milliseconds) to the glucose sensing electrode via the potientiostat 24. We prefer to use an EG&G Princeton Applied Research Model 384B Polarographic Analyzer.

In the technique we use, a symmetrical square wave is superimposed on a staircase wave form where the forward pulse of the square wave (pulse direction same as the scan direction) is coincident with the staircase step. The reverse pulse of the square wave occurs halfway through the staircase step. The current is sampled twice during each square wave cycle, once at the end of the forward pulse and once at the end of the reverse pulse.

This technique discriminates against charging or capacitance current by delaying the current measurement to the last 1.5 milliseconds or so of the pulse. The difference current between the two measurements is plotted versus the potential staircase. As a result, the pulse technique is more sensitive to oxidation or reduction currents, called Faradaic currents, than conventional DC voltammetry.

The differential pulse voltammetry yields peaks for Faradaic currents rather than a sigmoidal wave form of conventional DC voltammery. Similarly, square wave voltammetry yields peaks for Faradaic processes, and the peak height is directly proportional to the concentration of the species in solution. The current and voltage values as sensed by the electrode may be displayed on combined or separate ammeter and coulometer unit 27 of FIG. 2.

Pulsed coulometry is similar, except we measure the charge accumulated during the pulse. We integrate the current during the last 1.5 milliseconds or so of the pulse to focus on the purely oxidation and/or reduction currents.

The counter and working electrodes provide a varying current which is then plotted on the Y axis of a cyclic voltammogram in response to the current cycle impressed by the digital function (programmable pulse wave form) generator 23 and potentiostat 24. Similarly, the voltages of the reference and working electrodes are sampled throughout the domain in response to the voltage scan program of the digital function generator 23, and the output values are plotted on the X axis of the cyclic voltammogram.

FIGS. 3 and 4a show a series of superimposed cyclic voltammograms of increasing concentrations of carbohydrate in the above-identified in vitro situation. Vary sharp oxidation current peaks are seen at −0.72 V for glucose (FIG. 3) and −0.74 V for fructose (FIG. 4a); this is Peak 2. A reduction peak, Peak 1, is seen at −0.80

V for glucose (FIG. 3) and −0.84 V for fructose FIG. 4a). Both peaks are sharp, distinct, and reproduceable. As shown in FIGS. 3 and 4a, the peak height increases with increasing concentration, and the separation of the peaks is extremely clear. Unlike all other signals, the peak voltages of these two signals do not shift position (i.e. and drift free) with variation in carbohydrate concentrations. The absence of multiple or overlapping peaks in this region indicates that the chemistry is a simple redox. The two clear inflection points indicate the voltages at which the oxidation and reduction currents switch. For comparison to the carbohydrate cyclic voltammogram traces, FIGS. 3 and 4a show in dashed lines the trace for the electrolyte-alone buffer. Note the complete absence of peaks at −0.80 V and −0.84 V.

When the peak current height is plotted against carbohydrate concentration, the relationship is shown to be linear. As shown in FIGS. 4b, 5, 6, 7, 9 and 10, this linearity is clearly demonstrated for the medically useful range of 0–400 mg/dl and beyond. FIG. 4b shows the relationship for fructose in vitro for both peaks through the range of 600 mg/dl.

By the linearity of the plot, precise determinations of carbohydrate concentration can be determined by interpolation on the graph. This can be built into the programming of the output from the sensor (see FIGS. 1 and 2) so that there can be direct digital readout of carbohydrate concentration, which permits nearly instantaneous measurement of the concentration of carbohydrate sensed (glucose, fructose, mannose, etc.).

Similar results were obtained with both fructose and mannose. The concentrations of the carbohydrates were varied between 0 and 600 mg/dl in KRPB. A linear response of current versus carbohydrate concentration was obtained for both substances at both peaks 1 and 2 (−0.84 V and −0.74 V) with good sensitivity.

In vivo glucose sensor use was simulated by placing the electrode in human serum dialysate. Human serum (Sera-Chem, a normal clinical chemistry control serum from Fisher Scientific Company, Pittsburgh, PA) was dialysed against an equal volume of Krebs-Ringer phosphate buffer solution (KRPB) at pH 7.4, below −4° C. for over 24 hrs. The composition of the original serum, the dialysed serum, and the dialysate was determined by independent (conventional) analysis. Among others, interfering and/or inhibiting substances present in the dialysate included: urea, amino acids, creatinine, and uric acid. Both 50 and 100 ml volumes of the serum dialysate were placed in a testing cell of the type shown in FIG. 2. Cyclic voltammetric studies were carried out within a scan range of −0.80 V to +0.80 V versus Ag/AgCl at 30 mV/sec scan rate. We found that only the low potential redox signal peaks reported herein as Peaks 1 and 2 were uninhibited by substances present in the dialysate. While there is a minor alteration of the peaks, FIG. 5 shows that plots of the redox currents versus glucose concentrations of Peaks 1 and 2 are linear in the 100–200 mg/dl range. All other peaks that we had observed, in particular the peak at +0.70 V, were completely inhibited by substances present in the serum dialysate.

We have tested in serum dialysate beyond 500 mg/dl, and although precisely linear for such high concentrations, we have not found evidence of electrode poisoning or decrease in output. This is extremely important as it permits operation of in vivo, bedside, or extracorporeal infusion delivery system for patients in hyperglycemic shock, e.g. with glucose levels as high as 1000–1200 mg/dl. The sensor can sense "over limit" (out of normal range) conditions, and infuse relatively large amounts of insulin to quickly bring the values within range. Thereafter the system can sense glucose levels "on scale" within the normal 0–400 mg/dl range and can administrate innfusion at a preprogrammed rate to control the glucose level within a proper metabolic range.

FIG. 6 is a plot of the current peak heights for various concentrations of glucose in KRPB for the reduction peak, Peak 1, of −0.80 V, for both long scan times and short scan rates. The long scan is 30 mV/sec, whereas the short scan rate is 50 mV/sec. The linear relationship between glucose concentration and current peak height is clearly demonstrated by both scan rates.

FIG. 7 shows plots of the peak currents for Peaks 1 and 2 (−0.80 V and −0.72 V, respectively) with respect to the square roots of the scan rates. The linearity clearly demonstrates that the redox is under diffusion control. Further, since the curves (lines) follow the Randles-Sevcik relation very well, and the peak-to-peak separation at a scan rate of 30 mV/sec is 0.08 V at 37° C., the reaction can be considered a simple, direct, reversible, one electron transfer process which does not involve non-electrochemical or secondary reactions.

Figure 8:
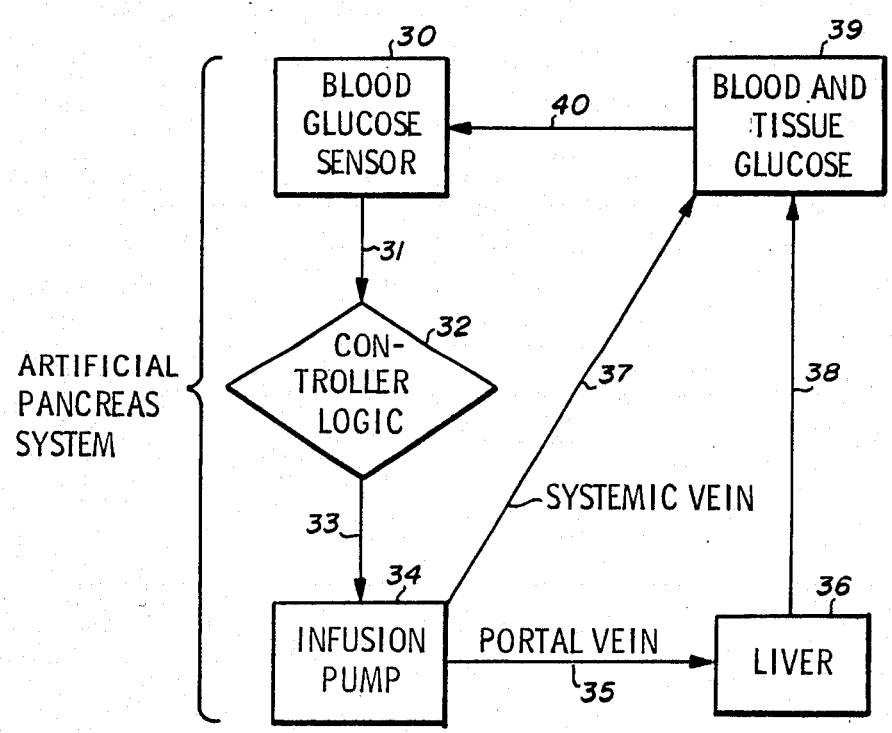
FIG. 8 is a schematic of an artificial pancreas system in accord with the principles of the invention.

FIG. 8 shows, in schematic form, an entire prosthetic system employing the glucose sensor of the present invention. The blood glucose sensor assembly (as described in more detail above in connection with FIGS. 1, and 2) may be implanted in vivo, for example, in contact with the blood stream, in contact with extracellular fluid, or directly in contact with tissue. The output signal 31, typically in digital form, is fed to a microprocessor controller which through preprogrammed logic compares the output signal to normal metabolic demand baseline. Where the glucose concentration is determined to be too low or too high, the appropriate amount of insulin, and possibly glucagon or glucose, may be metered into the blood stream by one or more infusion pump(s) 34 operating at the appropriate command signal 33 in response to the algorithm in the controller 32. The insulin may be input directly into the portal vein 35 to affect carbohydrate metabolism and glycogen storage in the liver 36 which restores the proper level of blood and tissue glucose 39 via normal circulation 38. When the blood glucose is low, glucagon and glucose can be directly metered through the systemic vein 37 to restore the blood and tissue glucose level 39. In turn, the blood glucose sensor assembly 30 continuously samples the flowing blood or tissue fluid 40 to maintain the proper physiologic control of metabolism in patients. Alternatively, insulin may be input into a body or tissue space such as the peritoneal cavity, a systemic vein, or the like.

FIGS. 9 and 10 demonstrate the sensor can precisely determine glucose concentration in the ultrafiltrate of human serum. In these figures, the concentration in mg/dl is plotted against the current in milliamperes for both Peaks 1 (FIG. 9) and 2 (FIG. 10) for a scan rate of 30 mV/sec. The temperature of the KRPB solution in which the glucose was dissolved was 37°±3° C.

It should be understood that various modifications within the scope of this invention can be made by one of ordinary skill in the art without departing from the spirit thereof. We therefore wish our invention to be defined by the scope of the appended claims as broadly as the prior art will permit, and in view of this specification if need be.

REFERENCES

1. Blackshear, P. J., Rohde, T. D., Grotting, J. C., Dorman, F. D., Perkins, P. R., Varco, R. L., Buchwald, H. *Diabetes.* 1979; 28: 634–639.
2. Bojsen, J., Deckert, T., Kolendorf, K., Lorup, B. *Diabetes.* 1979; 28: 974–979.
3. Champion, M. C., Shepherd, G. A. A., Rodger, N. W., Dupre, J. *Diabetes.* 1980; 29: 206–212.
4. Clemens, A. H. *Diabetes Care.* 1980; 3: 359–361.
5. Chang, K. W., Aisenberg, S., Soeldner, J. S., Heibert, J. M. *Trans. Am. Soc. Artif. Intern. Organs.* 1973; 19: 352–360.
6. Soeldner, J. S., Chang, K. W., Hiebert, J. M., Aisenberg, S. *Diabetes.* 1973; 24; 294.
7. Gough, D. A., Aisenberg, S., Colton, C. K., Giner, J., Soeldner, J. S. *Horm. Metab. Res. Suppl.* 1977; 7: 10–22.
8. Nalecz, M., Lewandowski, J., Werynski, A., Zawicki, I. *Artificial Pancreas.* 1978; 2: 305–309.
9. Gough, D. A., Anderson, F. L., Giner, J., Colton, C. K., Soeldner, J. S. *Anal. Chem.* 1978; 50: 941–944.
10. Rao, J. R., Richter, G. J., Luft, G., von Sturm, F. *Biomater. Med. Devices Artif. Organs.* 1978; 6(2): 127–49.
11. Marincic, L., Soeldner, J. S., Colton, C. K., Giner J., Morris, S. J. *Electrochem. Soc.* 1979; 126: 43–49.
12. Lerner, H., Giner, J. Soeldner, J. S., Colton, C. K. *J. Electrochem. Soc.* 1979; 126: 237–242.
13. Marincic, L. Soeldner, J. S., Giner, J., Colton, C. K. *J. Electrochem. Soc.* 1979; 126: 1687–1692.
14. Lemke, K., Gorner, M. *Bioelectrochem. Bioenerg.* 1981; 8: 115–124.
15. Updike, S. J., Hicks, G. P. *Nature.* 1967; 214: 986–988.
16. Bessman, S. P., Schultz, R. D. *Trans. Am. Soc. Artif. Intern. Organs.* 1973; 19: 361–364.
17. Silver, I. A. In: Kessler, M., Clark, L. C., Jr., Lubbers, D. W., Simon, W. Eds. *Ion and Enzyme Electrodes in Biology and Medicine.* Vol. 5: Munchen-Berlin-Wien: Urban and Schwarzenberg, 1976: 189.
18. Layne, E. C., Schultz, R. D., Thomas, L. J., Slama, G., Sayler, G. F., Bessman, S. P. *Diabetes.* 1976; 25: 81–89.
19. Bessman, S. P., Schultz, R. D. *Horm. Metab. Res.* 1972; 4: 413–417.
20. Clarke, W. L., Santiago, J. V. *Artificial Organs.* 1977; 1: 78–82.
21. Liu, C. C., Wingard, L. B., Wolfson, S. K., Jr., Yao, S. J., Drash, A. L., Schiller, J. G. *Bioelectrochem. Bioenerg.* 1979; 6: 19–26.
22. Clemens, A. H., Chang, P. H., Myers, R. W., *Horm. Metab. Res.* 1977; 7: 23–33.
23. Lerner, H., Giner, T., Soledner, J. S., Colton, C. K. Presented at the American Institute of Chemical Engineers, 1981 Annual Meeting, New Orleans, La., Nov. 8–12, 1981;
24. Guyton, J. R., Chang, K. W., Aisenberg, S., Soeldner, J. S. *Med. Instr.* 1975; 9: 227–232.
25. Giner, J., Marincic, L., Soeldner, J. S., Colton, C. K., *J. Electrochem. Soc.* 1981; 128: 2106–2114.
26. Lerner, H., Giner, J. D., Soeldner, J. S., 1982; U.S. Pat. No. 4,340,458.
27. Giner, J. D., Lerner, H., Soeldner, J. S., 1983; U.S. Pat. No. 4,396,464.

We claim:

1. An improved electrochemical redox sensor for precise in vitro and in vivo measurement of one or more carbohydrates present in organic and biological fluids and tissues by cyclic voltammetric or coulometric scanning, comprising in operative combination:
    (a) a cell having:
        (i) a first, working electrode adapted to permit contact with a test specimen of said carbohydrate being measured, said test specimen exhibiting at least one voltage peak upon said cyclic scanning;
        (ii) a second, counter electrode;
        (iii) a third, reference electrode;
        (iv) said working electrode being disposed to contact one or more carbohydrates present in a test specimen, and said second and said third electrodes being in ionic contact with each other and with said first electrode;
    (b) means for providing a current to said working electrode and withdrawing it from said counter electrode;
    (c) means for cyclic scan of said cell within a low potential far negative voltage domain of $-0.9$ V to $-0.2$ V vs. silver/silver chloride;
    (d) means for sensing the amount of current flow between said working and said counter electrodes for at least one voltage peak exhibited by said test specimen when scanned in said voltage domain, said voltage peak being selected from a cathodic reduction peak and an anodic oxidation peak, said peak being present in the range of about $-0.70$ V to $-0.90$ V vs. silver/silver chloride at 37 C; and
    (e) means for correlating said test specimen peak height sensed to a value of carbohydrate in said test specimen.

2. A sensor as in claim 1 wherein:
    (a) said scan rate controlling means includes means providing a pulsed scan at least at said voltage peak.

3. A sensor as in claim 2 which includes:
    (a) means for selectively controlling said scan rate in the range of from about 30 mV/sec to about 50 mV/sec.

4. A sensor as in claim 3 wherein:
    (a) said cyclic scan means includes means providing a steady sweep scan.

5. A sensor as in claim 2 which:
    (a) includes means for sampling current during the last about 1.5 milliseconds of said pulse at said peak.

6. A sensor as in claim 5 wherein said pulse duration is on the order of 20–50 milliseconds.

7. A sensor as in claim 6 wherein:
    (a) said working electrode is selected from wire, disc and metal film deposited on a biologically acceptable support.

8. A sensor as in claim 6 wherein:
    (a) said cell includes means for in vivo implantation comprising a tissue compatible material covering at least a portion of said first, working electrode.

9. A sensor as in claim 6 wherein:
    (a) said cell includes means for removably introducing at least said first, working electrode into a patient's body for positioning therein as an indwelling sensor for bedside monitoring.

10. A sensor as in claim 5 wherein:
    (a) said cell includes means for in vivo implantation comprising a tissue compatible material covering at least a portion of said first, working electrode.

11. A sensor as in claim 5 wherein:

(a) said cell includes means for removably introducing at least said first, working electrode into a patient's body for positioning therein as an indwelling sensor for bedside monitoring.

12. A sensor as in claim 2 wherein:
(a) said working electrode is selected from smooth platinum, platinum-black, palladium, palladium-black, rhodium, rhodium-black and alloys of platinum, iridium, and palladium.

13. A sensor as in claim 12 wherein:
(a) said cell includes means for in vivo implantation comprising a tissue compatible material covering at least a portion of said first, working electrode.

14. A sensor as in claim 12 wherein:
(a) said cell includes means for removably introducing at least said first, working electrode into a patient's body for positioning therein as an indwelling sensor for bedside monitoring.

15. A sensor as in claim 2 wherein:
(a) said cell includes means for in vivo implantation comprising a tissue compatible material covering at least a portion of said first, working electrode.

16. A sensor as in claim 2 wherein:
(a) said cell includes means for removably introducing at least said first, working electrode into a patient's body for positioning therein as an indwelling sensor for bedside monitoring.

17. A sensor as in claim 1 wherein:
(a) said cell includes means for in vivo implantation comprising a tissue compatible material covering at least a portion of said first, working electrode.

18. A sensor as in claim 1 wherein:
(a) said cell includes means for removably introducing at least said first, working electrode into a patient's body for positioning therein as an indwelling sensor for bedside monitoring.

* * * * *